March 9, 1976 W. A. WARRINER Plant Pat. 3,837
ROSE PLANT
Filed Dec. 13, 1974
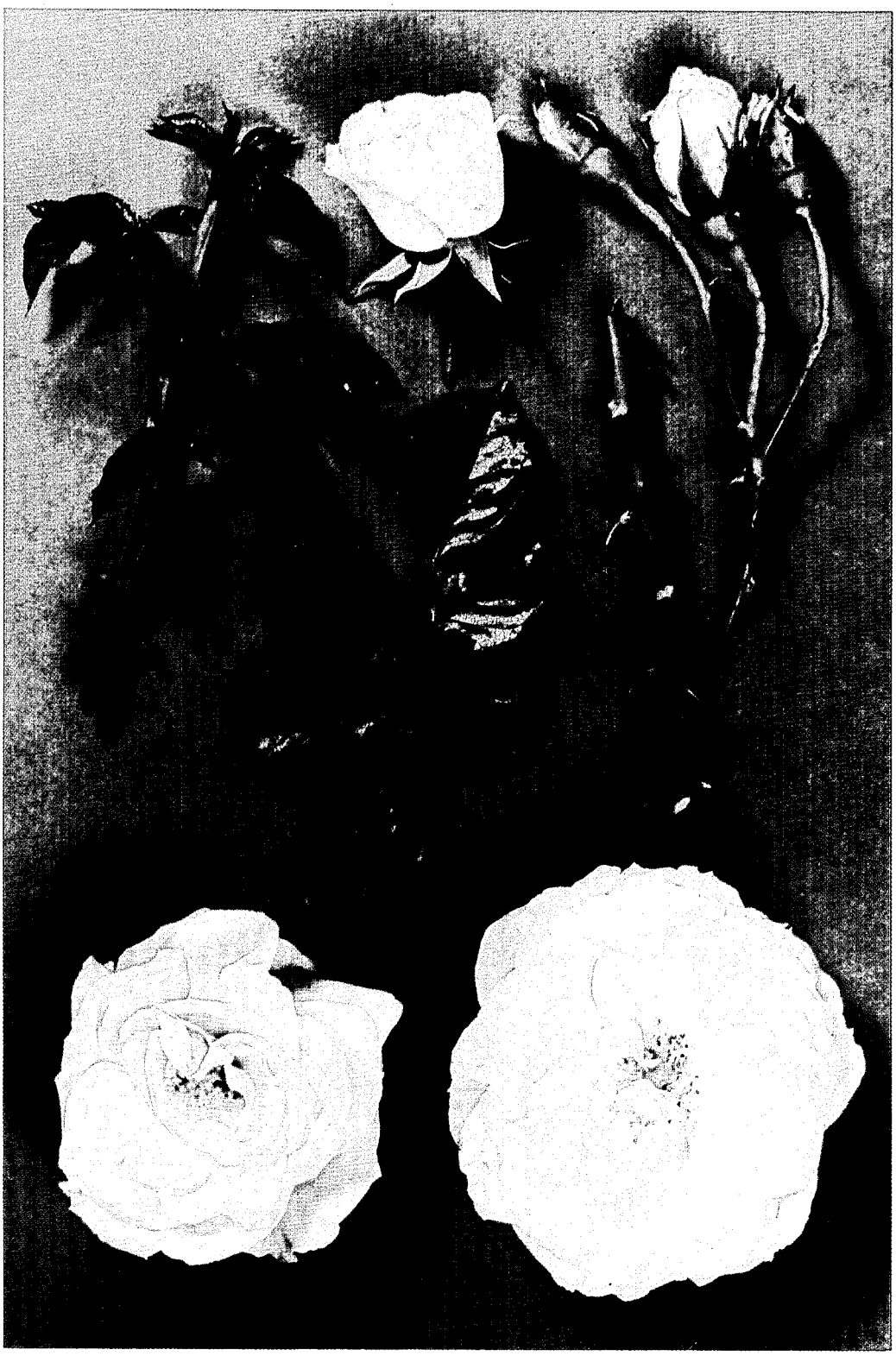

United States Patent

Plant Pat. 3,837
Patented Mar. 9, 1976

3,837
ROSE PLANT
William A. Warriner, Tustin, Calif., assignor to Jackson & Perkins Company, Medford, Oreg.
Filed Dec. 13, 1974, Ser. No. 532,702
Int. Cl. A01h 5/00
U.S. Cl. Plt.—5 1 Claim The present invention relates to a new and distinct cultivar of rose plant of the climber class which was originated by me by crossing two unnamed cultivars.

The primary objective of this breeding was to produce a cultivar of vigorous climbing characteristics, attractive foliage, large pink flowers that are produced throughout the growing season. This objective was substantially achieved along with other desirable traits as evidenced by the following unique combination of characteristics which are outstanding in the new cultivar and which distinguish it from its parents as well as from all other cultivars of which I am aware:

1. A very vigorous climbing habit of growth.
2. Production of clusters of flowers on the terminals of long, up to 12 feet or more, main canes in addition to production of flowers on secondary or lateral branches. Blooms are produced from early spring until stopped by cold weather in autumn.
3. Dark green, semi-glossy foliage which has moderately good resistance to rose powdery mildew.
4. Bud color of Chinese Coral (W) opening to four inch flowers of French Rose (W).
5. A slight fragrance.

Asexual reproduction of this new cultivar by budding, as performed at Wasco, Calif., shows that the foregoing characteristics and distinctions reproduce true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

Parentage: Seedling.
*Seed parent.*—Seedling of unnamed cultivar.
*Pollen parent.*—Unnamed cultivar.

Classification:
*Botanical.*—Rosa hybrid.
*Commercial.*—Climber.

FLOWER

Observations were made at Irvine, Calif., in October.

Blooming habit: Recurrent, continuous

Bud:
*Size.*—¾" to 1" when petals start to unfurl.
*Form.*—Ovoid.
*Color.*—When sepals first divide—near Chinese Coral (614/1) with large area near Chrome Yellow (605/2) at base of petal and blending to a color close to the lighter tint of Fire Red (15/3). When half blown; upper side of petals near Fire Red (15/2) with pronounced Chrome Yellow (605/1) base; lower side of petals near Chinese Coral (614/1) blending into large area of Chrome Yellow (605/1) at lower part of petal.
*Sepals.*—Color: Outer surface Scheeles Green (860/1) lightly shaded with Garnet Brown (00918/3). Inner surface Scheeles Green (860/3) with a light covering of white tomentum. Three appendaged sepals lightly appendaged. Two unappendaged sepals smooth edged.
*Receptacle.*—Color: Scheeles Green (860/1) shaded lightly with Garnet Brown (00918/3). Shape: Straight sided (cylindrical) with funnel shaped base. Size: Long. Surface: Smooth.
*Peduncle.*—Length: Short. Surface: Slightly prickly. Color: Light green. Strength: Bending, slender.
*Opening.*—Petals fold outwardly.

Bloom:
*Size.*—Large. Average size when fully expanded 4".
*Borne.*—In clusters, flat or irregular.
*Stems.*—Medium.
*Form.*—When first open, flat. Permanence—retains its form to the end.
*Petalage.*—Number of petals under normal conditions 25–30.
*Color.*—Center of flower: Upper side of petals French Rose (520/1). Base of petal blends to near White with a small area lighter than Chrome Yellow (605/2). Reverse side of petals French Rose (520/3). General tonality from a distance—French Rose (520 to 520/1).
*Discoloration.*—General tonality at end of first day—no change. Third day—color when petals fall is French Rose (520/3) after 4 or 5 days open on the plant.

Petals:
*Texture.*—Thick.
*Shape.*—Wide oval.
*Form.*—Tips slightly recurved.
*Arrangement.*—Loosely imbricated. Petaloids in center—few.
*Persistence.*—Drop off cleanly.
*Fragrance.*—Slight.
*Lastingness.*—On the plant—long. As cut flower—long.

Reproductive parts:
*Stamens, Anthers.*—Small, many. Color—Yellow. Arrangement—regular around styles.
*Filaments (Threads).*—Color—Yellow.
*Pollen.*—Gold Yellow.
*Styles.*—Color—nearly White.
*Stigmas.*—Color—light Yellow.

PLANT

Form: Climber.

Growth: Very vigorous. Climbing canes reach 9' to 15' in length terminating in a cluster of several blooms. Lateral branches produced from the main canes may be short stemmed or may also grow to several (up to 8) feet.

Foliage: Number of leaflets on normal mid-stem leaves, 5–7.
*Size.*—Medium.
*Quantity.*—Normal.
*Color.*—New foliage: Garnet Brown (00918). Old foliage: Parsley Green (00962).
*Shape.*—Oval.
*Texture.*—Semi-glossy.
*Edge.*—Serrated.
*Serration.*—Single, small.
*Petiole (rachis).*—Color—green. Underside—large prickles.
*Stipules.*—Long, smooth.
*Disease Resistance.*—Normally resistant to mildew under normal growing conditions at Irvine, Calif.

Wood:
*New Wood.*—Color—Light Green. Bark—smooth.
*Old Wood.*—Color—Green. Bark—smooth.

Prickles:

*Quantity.*—On main stalks from base—ordinary. On laterals from stalk—ordinary.

*Form.*—Broad based, hooked downward sharply.

*Color When Young.*—Brown.

*Position.*—Irregular.

Small Prickles:

*Quantity.*—On main stalks—few. On laterals—few.

*Color.*—Brown.

I claim:

1. A new and distinct cultivar of rose plant of the climber class, substantially as herein shown and described, characterized particularly as to novelty by the unique combination of its vigorous climbing habit of growth, dark green, semi-glossy foliage, buds of Chinese Coral (W) changing to French Rose (W) in the open flowers, and continuous blooming habit from spring through autumn.

No references cited.

ROBERT E. BAGWILL, Primary Examiner